United States Patent [19]

Hashimoto

[11] 3,974,167

[45] Aug. 10, 1976

[54] (7-NITRO-2-AZA-9-FLUORENYLIDENE) MALONONITRILE

[75] Inventor: Mitsuru Hashimoto, Tokyo, Japan

[73] Assignee: Ricoh Co., Ltd., Tokyo, Japan

[22] Filed: Dec. 30, 1974

[21] Appl. No.: 537,405

Related U.S. Application Data

[62] Division of Ser. No. 326,563, Jan. 24, 1973, Pat. No. 3,867,140.

[30] Foreign Application Priority Data

Jan. 24, 1972 Japan .................................. 47-9293

[52] U.S. Cl. .......................... 260/294.9; 260/297 R
[51] Int. Cl.$^2$ ........................................ C07D 221/06
[58] Field of Search .................................. 260/294.9

[56] References Cited

UNITED STATES PATENTS

| | | | |
|---|---|---|---|
| 3,796,572 | 3/1974 | Hashimoto | 96/1.5 |
| 3,867,140 | 2/1975 | Hashimoto | 260/294.9 |

OTHER PUBLICATIONS

Hashimoto, "Chem. Abstracts," vol. 79, (1973), No. 99206n.

Hashimoto, "Chem. Abstracts," vol. 80, (1974), No. 133287x.

*Primary Examiner*—Henry R. Jiles
*Assistant Examiner*—R. W. Ramsuer
*Attorney, Agent, or Firm*—Cooper, Dunham, Clark, Griffin & Moran

[57] ABSTRACT

Photosensitive material for use in electrophotography which is a charge transfer complex comprising (mononitro-2-aza-9-fluorenylidene) malononitrile and an organic photoconductor.

1 Claim, 1 Drawing Figure

(7-NITRO-2-AZA-9-FLUORENYLIDENE) MALONONITRILE

This is a division of application Ser. No. 326,563, filed Jan. 24, 1973, now U.S. Pat. No. 3,867,140.

BACKGROUND OF THE INVENTION

A. Field of the Invention

The present invention relates to novel compositions suitable for use in electrophotography.

B. Description of the Prior Art

Electrophotography is an art which usefully combines photoconductivity with electrostatic phenomena. A wide variety of inorganic substances as selenium, zinc oxide, and the like have heretofore been employed as photoconductors. Recently, however, organic photoconductive substances such as poly-N-vinyl carbazole and others have attracted wide attention. They are of particular interest because of their advantageous properties with respect to cost of production, transparency of product film, ease of film forming, etc. Despite these advantages, their wide adoption has been impeded because they are generally inferior to inorganic substances in sensitivity and exhibit only marginal sensitivities in the visible region of the spectra. This problem has been somewhat alleviated by the use of various sensitizing substances. Another problem which has retarded the adoption of organic photoconductors is that it is difficult to preserve them.

SUMMARY OF THE INVENTION

One object of the present invention is to provide organic photoconductive compositions which manifest useful sensitivity in the visible region of the spectrum.

Another object of the present invention is to provide organic photoconductive compositions which are superior in film transparency, film formability, preservability, etc. A principal feature of the invention is the provision of a charge transfer complex comprising a novel (mononitro-2-aza-9-fluorenylidene) malononitrile electron acceptor and any known organic photoconductive electron donor.

DETAILED DESCRIPTION OF THE INVENTION

Figure 1:
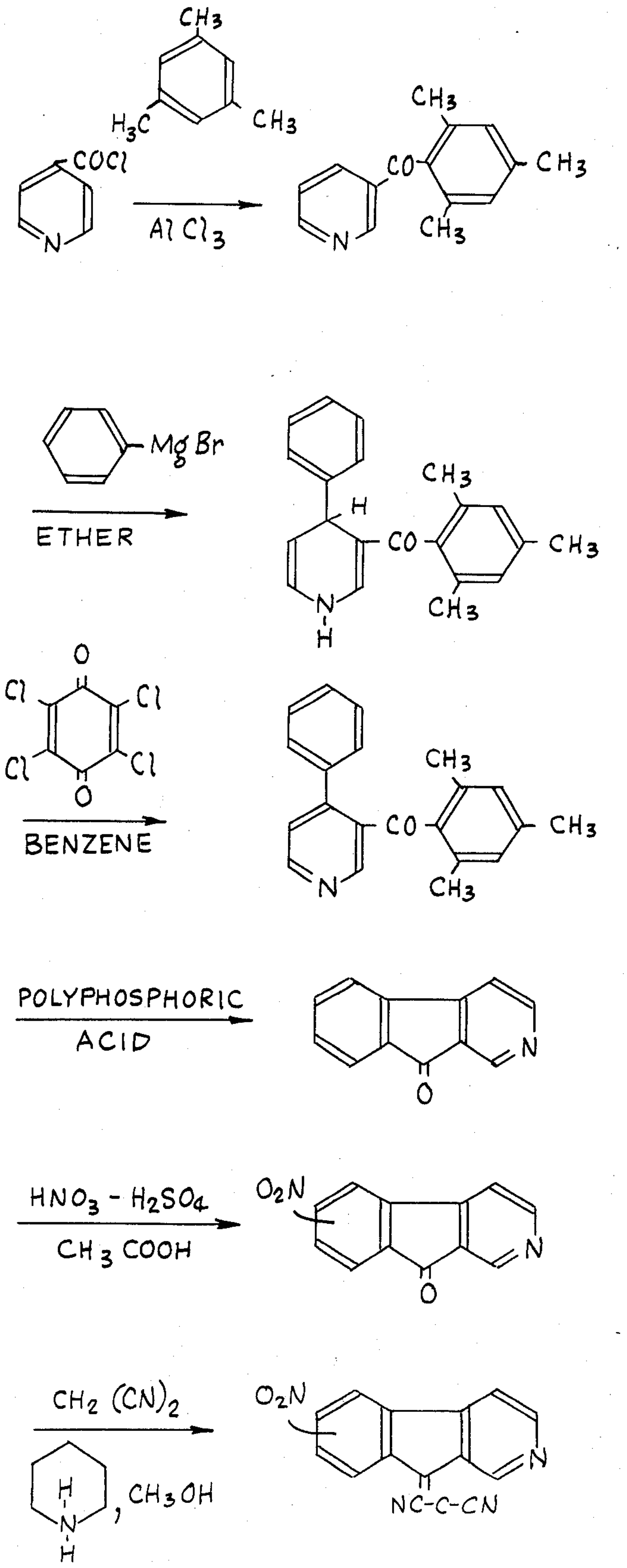

The above mentioned charge transfer complex comprising (mononitro-2-aza-9-fluorenylidene) malononitrile as the acceptor and various organic, photoconductive donors comprise the photoconductive compositions of the present invention. The compositions display panchromatic sensitivity and are useful with actinic light in the visible region of the spectrum. Their utility can be enhanced however by the addition of known sensitizers such as Rhodamine B, Rose Bengal, fluorescein and the like.

Preparation of electrophotographic compositions of the present invention can be easily effected by: mixing (mononitro-2-aza-9-fluorenylidene) malononitrile, the acceptor, with the selected donor in the weight ratio of from 1:100 to 150:100; adding such additives as may be desired such as binders, additional sensitizers and other conventional additives to the resulting mixture; dissolving the mixture in an appropriate inert, organic solvent such as dioxane, tetrahydrofuran, etc.; subsequently coating the thus obtained solution on an appropriate substrate. Suitable binders include, for example, novolak, acrylic resins and others of the type conventionally employed. Suitable substrates include, for example, aluminum plates, polyester films with a vacuum deposited aluminum layer, paper treated for conductivity, etc. The final product is dried.

Typically, a composition of the invention may contain added binder in the range of about 5 to 50 parts by weight relative to the total weight of the mixture, and additional sensitizers such as fluorescein in the weight range of about 0.001 to 0.01 parts by weight based on the weight of the donor.

Typical donors which may be employed in this invention include condensation polycyclic compounds such as pyrene, perylene, anthracene, etc., phenothiazine, phenoxazine, thionine, 9,9-diphenyl-9,10-dihydroanthracene, 2,3-diphenyl pyrrocoline, α,ω-bis(N-carbazolyl)-propane, N,N,N',N'-tetrabenzyl-P-phenylene diamine, 1,6-dimethoxyphenazine, 1,8-bis(dimethylamino)-naphthalene, 1,1,5-triphenylbrom-1-en-4-in-3-ol, N-ethyl carbazole, N-propyl carbazole, 3,6-dibrom-N-ethyl carbazole, 2-phenyl-3-P-dimethylaminophenyl quinoxaline, acridine, p,p'-bis-dimethylamino biphenyl, p,p'-bisdiphenylamino biphenyl, 2,3,4,5-tetrakis (p-dimethylaminophenyl)-pyrrole, 2-p-dimethylaminophenyl-3,4-diphenyl imidazole, 2,5-bis(p-dimethylaminophenyl)-1,3,4-oxadiazole, 4-phenyl-5-p-dimethylaminophenyl-3H-2-imidazolone, etc., and, as high-molecular compounds, there may be poly-N-vinyl carbazole, poly-3-vinyl-N-ethyl carbazole, polyphenylene pyrazole, poly-1-allyl-4,5-diphenyl imidazole, polyvinyl pyrene, polyvinyl phenanthrene, polyacenaphthylene, poly-N-vinyl-3,6-dibromocarbazole, polyvinyl dibenzothiophene, poly-9-vinyl acridine, poly-N-allyl phenothiazine, poly-P-imidazolyl-(2)-styrene, polyvinyl anthracene, poly-P-phenylene-1,3,4-oxadiazole, anthracene-formalin condensation resin, polypyromellitimide, vinyl anthracene-N-vinyl carbazole copolymer, 1,2-dihydroacenaphthene-indene copolymer, pyrene-formalin condensate, polyvinyl Malachite Green, polyvinyl dibenzofuran, poly-2-vinyl quinoline, poly-2-vinyl furan, poly-3-benzofuran, poly-2-vinyl-4-(4'-dimethyl aminophenyl)-3-phenyl oxazole, as well as reaction products between polyvinyl amine and anthracene-9-aldehyde, naphthalene-formalin resins, N-ethyl carbazole-formalin resins, etc.

The (mononitro-2-aza-9-fluorenylidene) malononitrile for use in the present invention can be synthesized by the following procedure:

First, by effecting Friedel Krafts reaction between hydrochloride nicotinic acid chloride and mesitylene in accordance with Reynold C. Fuson and John J. Miller's method [cf. J.Am.Chem. Soc. 79.3477 (1957)], 3-mesitol pyridine (yield: 63%, b.p.:157.5°–158°C/4mmHg) is obtained.

Next, by phenylizing this reaction product through Grignard's reaction, 3-mesitol-4-phenyl-dihydropyridine (yield: 76%, m.p.:183°–185.5°C; light yellow powder) is obtained. Further, by oxidizing this product with chloranil in benzene, 3-mesitol-4-phenyl pyridine is obtained.

When the thus obtained compound is subjected to ring formation by utilizing polyphosphoric acid, there is obtained 2-aza-9-fluorenone to serve as the material. Then by reacting this material with mixed sulfuric and nitric acids in an acetic acid solvent at a temperature of about 90°C for 1 hour, mononitro-2-aza-9-fluorenone which is principally the 7-nitrated product is obtained.

Subsequently, by making this mononitro-2-aza-9-fluorenone react with malononitrile in methanol in the presence of piperidine as catalyst, the intended (mononitro-2-aza-9-fluorenylidene) malononitrile is obtained. The reactions are shown in FIG. 1.

The photosensitive compositions of this invention comprising a charge transfer complex containing (mononitro-2-aza-9-fluorenylidene) malononitrile and an organic photoconductive donor as the principal components are sensitive in the visible region of the spectrum, have satisfactory preservability and reproducibility, and are further applicable to the transfer process. When deposited on an electrically conductive substrate they form excellent electrophotographic plates.

The following non-limiting examples are given by way of illustration only:

EXAMPLE 1

A solution obtained by dissolving 64 mg of poly-N-vinyl carbazole, 91 mg of (7-nitro-2-aza-9-fluorenylidene) malononitrile and 100 mg of diphenyl chloride in 10 g of tetrahydrofuran is coated by means of a doctor blade having wet gaps of 200$\mu$, on an aluminum coated Mylar film and dried to produce an electrophotographic plate having a photosensitive film layer about 10 microns thick.

Subsequently, the thus prepared plate is charged by means of corona discharge (−6KV), exposed to light by means of an apparatus equipped with a tungsten lamp capable of producing an intensity of illumination on the sensitive surface of the plate of 3 luxes and measured for its surface potential, whereby the time required for decreasing said potential to half (hereinafter referred to as exposure time required for half decay) is measured. It was found that the exposure time required for half decay is about 4 seconds.

Similar results are obtained with poly-N-vinyl-3,6-dibromocarbazole and poly-N-vinyl-3′-chlorocarbazole.

EXAMPLE 2

A solution is prepared by dissolving 900 mg of poly-N-vinyl-3-bromocarbazole, 91 mg of (7-nitro-2-aza-9-fluorenylidene) malononitrile and 100 mg of diphenyl chloride in 15 g of tetrahydrofuran. When this composition is treated in the same manner as the compositions of Example 1 it is found that the exposure time required for half decay is about 3.5 seconds.

EXAMPLE 3

A sensitive material is prepared in the same way as in Example 1 except for increasing the amount of (7-nitro-2-aza-9-fluorenylidene) malononitrile to 910 mg from 91 mg as employed in Example 1. The exposure time required for half decay of this sensitive material is about 1.5 seconds.

EXAMPLE 4

A sensitive material is prepared in the same way as in Example 2 except for increasing the amount of (7-nitro-2-aza-9-fluorenylidene) malononitrile to 910 mg from 91 mg as employed in Example 1. The exposure time required for half decay of this sensitive material is about 1.4 seconds.

EXAMPLE 5

A sensitive material is prepared by adding 500 mg of (7-nitro-2-aza-9-fluorenylidene) malononitrile to 1,000 mg of pyrene-formalin resin. The exposure time required for half decay of this sensitive material is about 2 seconds.

What is claimed is:

1. (7-Nitro-2-aza-9-fluorenylidene) malononitrile.

* * * * *